US012478165B2

(12) United States Patent
Park et al.

(10) Patent No.: US 12,478,165 B2
(45) **Date of Patent: *Nov. 25, 2025**

(54) PACKAGING KIT FOR COSMETIC FORMULATION

(71) Applicant: L'Oreal, Paris (FR)

(72) Inventors: Kyoo Jin Park, Leonia, NJ (US); Zachary John Mahoney, Freehold, NJ (US); Erika Menoni, Hazlet, NJ (US); Caroline Guetta-Ohayon, Englewood, NJ (US); Laura Martone, Wall, NJ (US); Eric de Bardonneche, Montaren-et-Saint-Mediers (FR)

(73) Assignee: L'Oreal, Paris (FR)

( * ) Notice: Subject to any disclaimer, the term of this patent is extended or adjusted under 35 U.S.C. 154(b) by 268 days.

This patent is subject to a terminal disclaimer.

(21) Appl. No.: 17/852,621

(22) Filed: Jun. 29, 2022

(65) Prior Publication Data

US 2023/0000234 A1 Jan. 5, 2023

Related U.S. Application Data

(60) Provisional application No. 63/216,714, filed on Jun. 30, 2021.

(30) Foreign Application Priority Data

Aug. 19, 2021 (FR) ....................................... 2108764

(51) Int. Cl.
*A45D 34/04* (2006.01)
*A46B 9/02* (2006.01)
(Continued)

(52) U.S. Cl.
CPC ............ *A45D 34/046* (2013.01); *A46B 9/021* (2013.01); *A61K 8/064* (2013.01); *A61K 8/88* (2013.01);
(Continued)

(58) Field of Classification Search
CPC .. A46B 9/00; A46B 9/02; A46B 9/021; A46B 9/025; A46B 9/026; A46B 9/028;
(Continued)

(56) References Cited

U.S. PATENT DOCUMENTS

| | | | | |
|---|---|---|---|---|
| 2005/0061349 A1 | | 3/2005 | Patel et al. | |
| 2006/0289027 A1 | * | 12/2006 | Wyatt .................. | A45D 40/262 132/218 |

(Continued)

OTHER PUBLICATIONS

France Search Report and Written Opinion mailed Apr. 28, 2022, issued in Application No. FR2108764, filed Aug. 19, 2021, 9 pages.

(Continued)

*Primary Examiner* — Rachel R Steitz
*Assistant Examiner* — Karim Asqiriba
(74) *Attorney, Agent, or Firm* — Christensen O'Connor Johnson Kindness PLLC

(57) ABSTRACT

A mascara packaging set includes a container with a wiper having an aperture and a mascara composition stored within the container. The mascara composition includes a wax emulsion, at least one polymer, and fibers and has a viscosity in a range of 10,000 cps to 20,000 cps. The kit also includes an applicator configured to extend into the container through the aperture. The applicator has an elongate core and bristles extending radially therefrom. At least one of the bristles is formed from a thermoplastic elastomer having a hardness in the range of 32 shore D to 38 shore D. The bristles form rows along the core in an axial direction, wherein rows of a first pair of adjacent rows are spaced farther apart from each other in a circumferential direction than a second pair of adjacent rows. The first pair of adjacent rows define a reservoir.

17 Claims, 3 Drawing Sheets

(51) Int. Cl.
*A61K 8/06* (2006.01)
*A61K 8/88* (2006.01)
*A61Q 1/10* (2006.01)

(52) U.S. Cl.
CPC .......... *A61Q 1/10* (2013.01); *A46B 2200/106* (2013.01); *A61K 2800/87* (2013.01)

(58) Field of Classification Search
CPC ................ A46B 9/065; A46B 2200/00; A46B 2200/1046; A46B 2200/1053; A46B 2200/106; A45D 34/00; A45D 34/042; A45D 34/043; A45D 34/045; A45D 34/046; A45D 34/047; A45D 34/04; A61K 8/06; A61K 8/062; A61K 8/064; A61K 8/066; A61K 8/068; A61K 8/88; A61K 2800/87; A61Q 1/10
See application file for complete search history.

(56) References Cited

U.S. PATENT DOCUMENTS

2008/0011317 A1* 1/2008 Malvar .................. A46B 9/021 15/207.2
2012/0060859 A1* 3/2012 Wyatt .................. A61K 8/8111 132/218
2013/0000663 A1 1/2013 Jacob et al.
2014/0105667 A1* 4/2014 Castex ................. A45D 40/265 132/218
2015/0174056 A1* 6/2015 Barba .................... A61K 8/375 424/70.7
2015/0327654 A1* 11/2015 Pires .................... A45D 40/262 401/118
2017/0258203 A1* 9/2017 Crane .................. A45D 40/262
2017/0347776 A1* 12/2017 Jacob ....................... A46B 3/18
2017/0347784 A1* 12/2017 Jacob ....................... A46B 3/18
2018/0344016 A1* 12/2018 Motornov ............ A61K 8/8152
2020/0069038 A1* 3/2020 Li ............................ A61Q 1/10

OTHER PUBLICATIONS

International Search Report and Written Opinion mailed Oct. 11, 2022, issued in corresponding International Application No. PCT/US2022/035593, filed Jun. 29, 2022, 16 pages.

* cited by examiner

PACKAGING KIT FOR COSMETIC FORMULATION

CROSS REFERENCE TO RELATED APPLICATIONS

This application claims the benefit of Provisional Application No. 63/216,714, filed Jun. 30, 2021. This application also claims priority to French Application No. 2108764, filed Aug. 19, 2021. The entire disclosures of both applications are hereby incorporated by reference herein for all purposes.

TECHNICAL FIELD

Embodiments of the present disclosure relate to a packaging kit for cosmetic compositions applied to keratin fibers. In some embodiments, the packaging kit includes an applicator with particular material properties advantageous for applying cosmetic compositions having specific chemical properties.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In accordance with an aspect of the present disclosure, a mascara packaging set is provided. In an embodiment, the set includes a container with a wiper having an aperture and a mascara composition stored within the container. The mascara composition includes a wax emulsion, at least one polymer, and fibers and has a viscosity in a range of 10,000 cps to 20,000 cps. The kit also includes an applicator configured to extend into the container through the aperture. The applicator has an elongate core and bristles extending radially therefrom. At least one of the bristles is formed from a thermoplastic elastomer having a hardness in the range of 32 shore D to 38 shore D. The bristles form rows along the core in an axial direction, wherein rows of a first pair of adjacent rows are spaced farther apart from each other in a circumferential direction than a second pair of adjacent rows. The first pair of adjacent rows define a reservoir.

In any embodiment, the bristles from the first pair of rows have a semi-circular cross-sectional area.

In any embodiment, the bristles from the second pair of rows have polygonal cross-sectional area.

In any embodiment, the bristles from the second pair of rows have circular cross-sectional area In any embodiment, the aperture of the wiper is sized to limit a thickness of a layer of mascara composition on the brush to a predetermined maximum thickness when the brush is removed from the container.

In any embodiment, the maximum thickness is in the range of 1.20 mm to 1.50 mm.

In any embodiment, the aperture has a diameter in the range of 4.00 mm to 5.00 mm.

In any embodiment, at least one row of bristles is formed from a different material than at least one of the other rows of bristles.

In any embodiment, the at least one row of bristles is more rigid than the at least one of the other rows of bristles.

In any embodiment, the at least one row of bristles is formed by the thermoplastic elastomer and a second material.

In any embodiment, the second material has a hardness greater than the harness of the thermoplastic elastomer.

In any embodiment, the wax emulsion comprises a water-in-wax emulsion.

In any embodiment, the polymer has a weight-average molecular mass of less than 100,000.

In any embodiment, the polymer has a weight-average molecular mass of less than 50,000.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

The present disclosure relates to applicators for applying a cosmetic product, and in particular, applicators for applying formulations of known cosmetic products to keratin fibers, in particular eyelashes or eyebrows, for example mascara. Applicators of this type generally take the form of a brush having an elongate central core with a plurality of bristles extending radially therefrom. Embodiments of the disclosed and claimed subject matter may be described herein in with reference to mascara and brushes for applying the same, however, it will be appreciated that the disclosure is not limited to mascara and brushes. In this regard, the term "mascara" more generally includes cosmetic formulations of the type described herein to be applied to keratin fibers. Further, as used herein, the term "brush" is not limited to a particular applicator configuration and may include various configurations having a plurality of bristles extending from a core.

It is desirable that the mascara brushes be configured to retain a sufficient amount of product, i.e., cosmetic formulation, so that it is not necessary to recharge the brush too often during application. Further, these applicators must make it possible to grasp the lashes, to separate the lashes, to lengthen the lashes, and/or to bend the lashes, according to the type of makeup desired. Known applicators, such as mascara brushes or combs, have fixed characteristics with regard to flexibility and the arrangement in the space of the bristles or teeth. For example, known applicators typically have a hardness in the range of 45 shore A to 55 shore A.

The performance of a mascara usually is less dependent on the brush itself or the formula itself, but instead depends on the specific combinations of brush/material/wiper/formula being used. Some combinations of specific dimensions/material hardnesses/formula viscosities/etc., will deliver performance superior to competition with similar brushes and/or similar formulations but missing one or more of the key attributes. The present disclosure describes combinations not formerly practiced in the industry.

Figure 1:
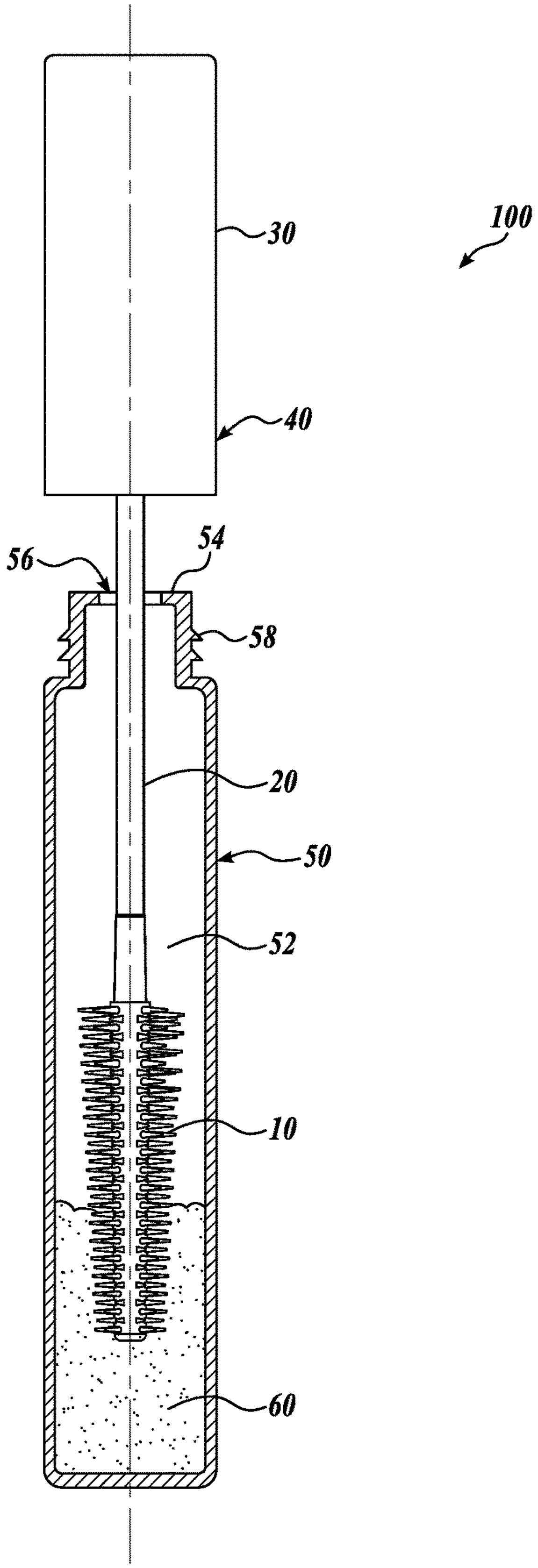
FIG. 1 shows a cross-sectional view of a representative embodiment of cosmetic product kit according to the present disclosure.

FIG. 1 shows packaging set 100 for a cosmetic composition 60 according to aspects of the present disclosure. The set 100 includes a container 50 with an interior cavity in which the cosmetic composition 60 is stored. An opening is formed in the container and is covered by a wiper 54 with an aperture 56 extending therethrough.

An applicator 40 includes a handle 30 that engages threads 58 formed on the container 50 to detachably couple the applicator to the container. An elongate stem 52 extends from the handle 30 and includes a brush 10 positioned on the end of the stem opposite the handle. When the handle 30 of the applicator 40 is coupled to the container 50, the stem 20 extends through the aperture 56 of the wiper 54, and the handle covers the aperture to seal the interior of the container. At the same time, the brush 10, which will be described in further detail, is positioned within the container 50 and in contact with the cosmetic composition 60 disposed therein.

Suitable embodiments of a cosmetic composition according to the present disclosure may comprise a wax and a polymer. According to a first embodiment, the composition comprises, in a physiologically acceptable medium, a wax and a polymer with a specific amide unit, intended in particular for the cosmetic field. In an embodiment, the composition is in the form of a composition for coating the eyelashes (in particular mascara), eyeliner, product for the eyebrows, product for the lips, blush or eyeshadow, foundation, body makeup product, concealer, nail polish, skin care product, including scalp, hair product (hair mascara, spray). The composition can also be applied to make-up accessories (support) such as false eyelashes, hairpieces, wigs, false nails or else on sticks or patches adhering to the skin or hares (of the fly type).

In the composition, the use of a polymer with a particular amide unit in combination with a wax-in-water emulsion makes it possible to improve the adhesion properties of the composition on keratinous materials, in particular on keratin fibers such as eyelashes. The composition is easily applied to keratinous materials and allows the composition to be deposited quickly in sufficient quantity to obtain a makeup having the expected cosmetic properties. In particular, a thick deposit of make-up is quickly obtained on the keratinous materials, which prevents users from applying the composition for too long to the keratinous materials. Thus, for a mascara, a makeup is obtained that rapidly thickens the keratin fibers, in particular the eyelashes; there is thus an instantaneous loading of the eyelashes. In addition, the mascara gives good lengthening to the made-up eyelashes.

In some embodiments, the composition may comprise, in a physiologically acceptable aqueous medium, a wax-in-water emulsion and at least one first polymer of weight average molecular weight less than 100,000, comprising a polymer backbone, having non-pendant amide units and at least one pendant fatty chain and/or at least one terminal fatty chain optionally functionalized, having from 6 to 120 carbon atoms and being linked to these amide units.

In some embodiments, the composition may include a combination of at least one first polymer of weight-average molecular mass of less than 100,000 and better still less than 50,000, comprising a) a polymer backbone having repeating hydrocarbon patterns provided with at least one non-pendant amide unit, and at least one pendant fatty chain and/or at least one terminal fatty chain optionally functionalized, having from 6 to 120 carbon atoms and being linked to these amide units, and at least at least one wax, in a physiologically acceptable composition in the form of a wax-in-water emulsion, for obtaining an adherent deposit on keratinous materials and/or for rapid makeup of keratinous materials and/or for rapidly thickening and/or lengthening the eyelashes.

As used herein, a "physiologically acceptable medium" is a non-toxic medium capable of being applied to the skin, the integuments, or the lips of human beings, such as a cosmetic medium.

As used herein, a "functionalized chain" is an alkyl chain comprising one or more functional or reactive groups chosen in particular from amide, hydroxyl, ether, oxyalkylene or polyoxyalkylene, halogen groups, including fluorinated or perfluorinated groups, ester, siloxane, polysiloxane. In an embodiment, the hydrogen atoms of one or more fatty chains are substituted at least partially by fluorine atoms. In an embodiment, these chains are linked directly to the polymer backbone or via an ester function or a perfluorinated group.

As used herein, a "polymer" is a compound having at least 2 repeating units, and preferably at least 3 repeating units.

As used herein, a "hydrocarbon repeating unit" is a unit comprising from 2 to 80 carbon atoms, and preferably from 2 to 60 carbon atoms, carrying hydrogen atoms and optionally atoms of oxygen, which, in an embodiment, are linear, branched or cyclic, saturated or unsaturated. These units further comprise each of one or more non-pendant amide units found in the polymer backbone.

In an embodiment, the pendant chains are linked directly to at least one of the amide units of the polymer backbone.

In an embodiment, the first polymer comprise, between the hydrocarbon units, silicone units or oxyalkylene units.

In addition, in some embodiments, the first polymer of the composition can include from 40% to 98% of fatty chains relative to the total number of amide units and fatty chains and better still from 50% to 95%. The proportion of amide patterns may depend on the nature of the fatty phase and is in particular similar to the polar nature of the fatty phase. Thus, the higher the proportion of amide units in the first polymer, which corresponds to the presence of several amide units, the more the first polymer has affinity with polar oils.

In an embodiment, the first polymer of the composition has a weight-average molecular mass of less than 100,000 (in particular ranging from 1,000 to 100,000), in particular less than 50,000 (in particular ranging from 1000 to 50,000), and more particularly ranging from 1,000 to 30,000, preferably 2000 to 20,000, and better from 2000 to 10,000.

The first polymer, and in particular polyamide, is not soluble in water, in particular at 25° C. In particular, the first polymer does not contain an ionic group.

As first preferred polymers used in an embodiment, mention may be made of polyamides branched by pendant fatty chains and/or fatty terminal chains having from 6 to 120 carbon atoms and better still from 8 to 120 and in particular from 12 to 68 carbon atoms, each terminal fatty chain being linked to the polyamide skeleton by at least one linking group, in particular an ester.

Preferably, these polymers comprise a fatty chain at each end of the polyamide skeleton. As other linking group, mention may be made of the ether, amine, urea, urethane, thioester, thiurea, thiourethane groups.

These polymers are more especially those described in U.S. Pat. No. 5,783,657, "ESTER-TERMINATED POLYAMIDES OF POLYAMERIZED FATTY ACIDS USEFUL IN FORMULATING TRANSPAREENT GELS IN LOW POLARITY LIQUIDS," ("the '657 patent"), the disclosure of which is incorporated by reference herein.

Each of these polymers satisfies in particular the following formula (I):

(I)

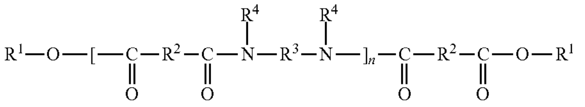

wherein n denotes an integer number of amide units such that the number of ester groups represents from 10% to 50% of the total number of ester and amide groups; $R^1$ is independently at each occurrence an alkyl or alkenyl group having at least 4 carbon atoms and in particular from 4 to 24 carbon atoms; $R^2$ represents independently at each occurrence a $C_4$ to $C_{42}$ hydrocarbon group provided that 50% of the $R^2$ groups represent a $C_{30}$ to $C_{42}$ hydrocarbon group; $R^3$ independently represents at each occurrence an organic group provided with at least 2 carbon atoms, hydrogen atoms and optionally one or more oxygen or nitrogen atoms; and $R^4$ independently represents, at each occurrence, a hydrogen atom, a $C_1$ to $C_{10}$ alkyl group or a direct bond to $R^3$ or another $R^4$ so that the nitrogen atom to which both $R^3$ and $R^4$ are bonded part of a heterocyclic structure defined by $R^4$—N—$R^3$, with at least 50% of $R^4$ representing a hydrogen atom.

In the case of formula (I), in an embodiment, the terminal fatty chains optionally functionalized are terminal chains linked to the last nitrogen of the polyamide skeleton.

The ester groups of formula (I), which are part of the terminal and/or pendant fatty chains within the meaning of the invention, may represent from 15% to 40% of the total number of ester and amide groups and better still from 20% to 35%. In addition, in some embodiments, n may advantageously represent an integer ranging from 1 to 5 and better still greater than 2. Preferably, $R^1$ is a $C_{12}$ to $C_{22}$, and preferably, $C_{16}$ to $C_{22}$. In an embodiment, $R^2$ are advantageously a $C_{10}$ hydrocarbon (alkylene) group with $C_{42}$. Preferably, at least 50% and better still at least 75% of the Rs are groups having from 30 to 42 carbon atoms. The other $R^2$ are hydrogenated groups at $C_4$ to $C_{19}$, and even at $C_4$ to $C_{12}$. Preferably, $R^3$ represents a $C_2$ to $C_{36}$ hydrocarbon group or a polyoxyalkylenated group and $R^4$ represents a hydrogen atom. Preferably, $R^3$ represents a hydrocarbon group in $C_2$ to $C_{12}$.

In an embodiment, the hydrocarbon groups are linear, cyclic or branched, saturated or unsaturated groups. Furthermore, in an embodiment, the alkyl and alkylene groups are linear or branched groups, saturated or not.

In general, the polymers of formula (I) are in the form of polymer blends, these blends can also contain a synthetic product corresponding to a compound of formula (I) where n is 0, that is to say a diester.

The terminal ester groups result from the esterification of the remaining acid terminations by alcohol cetyl, stearyl or mixtures thereof (also called cetylstearyl alcohol).

As the first polymer used in an embodiment, mention may also be made of polyamide resins resulting from the condensation of an aliphatic di-carboxylic acid and a diamine (including compounds having more than 2 carbonyl groups and 2 amine groups), the carbonyl and amine groups of adjacent unitary units being condensed by an amide bond. In some embodiments, these polyamide resins have a weight average molecular weight ranging from 6000 to 9000.

Exemplary embodiments of polyamides are disclosed in U.S. Pat. No. 5,500,209, "DEODORANT AND ANTIPERSPIRANT COMPOSITIONS CONTAINING POLYAMIDE GELLING AGENT," the disclosure of which is incorporated by reference herein.

It is also possible to use polyamide resins obtained from vegetables such as those described in the '657 patent and U.S. Pat. No. 5,998,570, "ESTER-TERMINATED POLYAMIDES OF POLYAMERIZED FATTY ACIDS USEFUL IN FORMULATING TRANSPAREEENT GELS IN LOW POLARITY LIQUIDS," the disclosure of which is incorporated by reference herein.

The first polymer present in the composition according to the disclosure advantageously has a softening temperature greater than 65° C. and possibly up to 190° C. Preferably, the first polymer has a softening temperature ranging from 70° C. to 130° C. and better still from 80° C. to 105° C.

The first polymer is in particular a non-waxy polymer.

The first polymer may correspond to the formula (I) mentioned above. This first polymer has good solubility in oils because of the fatty chain(s), and therefore, lead to macroscopically homogeneous compositions even with a high rate (at least 25%) of polymer, unlike polymers free from fatty chains.

In an embodiment, the first polymer is present in the composition in a content ranging from 0.01% to 10% by weight, relative to the total weight of the composition, preferably ranging from 0.05% to 5% by weight, and better ranging from 0.1% to 3% by weight.

The fatty phase of the composition may comprise a wax. As used herein, "wax" means a lipophilic fatty compound, solid at room temperature (25° C.) and atmospheric pressure (760 mm Hg, or $10^5$ Pa), with reversible solid/liquid state change, having a melting temperature above 30° C. and better still above 55° C. and possibly up to 200° C., in particular up to 120° C.

In an embodiment, the waxes present in the composition are dispersed in the form of particles in an aqueous medium. These particles can have an average size ranging from 50 nm to 10 μm, and preferably from 50 nm to 3.5 μm.

In particular, in an embodiment, the wax is present in the form of a wax-in-water emulsion, the waxes being able to be in the form of particles of average size ranging from 1 μm to 10 μm, and preferably from 1 μm to 3.5 μm.

In another embodiment of the composition according to the invention, the wax is present in the form of a microdispersion of wax, the wax being in the form of particles whose average size is less than 1 and ranges in particular from 50 nm to 500 nm.

In an embodiment, the wax is present in the composition in a content ranging from 0.1% to 50% by weight, relative to the total weight of the composition, preferably from 0.5% to 30% by weight, and better from 1% to 20% by weight.

In an embodiment, the first polymer and the wax are advantageously present in the composition according to a wax/first polymer weight ratio ranging from 5 to 60, preferably ranging from 7 to 50, and better still from 10 to 40.

The aqueous phase constitutes the continuous phase of the composition. The aqueous phase can comprise essentially water. The aqueous can also comprise a mixture of water and water-miscible solvent (miscibility in water greater than 50% by weight at 25° C.) such as lower monoalcohols having from 1 to 5 carbon atoms such as ethanol, isopropanol, glycols having from 2 to 8 carbon atoms such as propylene glycol, ethylene glycol, 1,3-butylene glycol, dipropylene glycol, $C_3$-$C_4$ ketones, $C_2$-$C_4$ aldehydes. In an embodiment, the water-miscible solvent is present in a content ranging from 0.1% to 20% by weight, relative to the total weight of the composition, and preferably ranging from 0.1% to 10% by weight. In particular, the content of water-miscible organic solvent represents from 0.1% to 30% of the weight of water present in the composition.

In an embodiment, the aqueous phase (water and optionally the organic solvent miscible with water) is present, in a content ranging from 1% to 95% by weight, relative to the total weight of the composition, preferably from 5% to 80% by weight, and better still from 10% to 60% by weight.

The composition according to the invention may contain emulsifying surfactants present in particular in a proportion ranging from 2% to 30% by weight relative to the total weight of the composition, and better still from 5% to 15%. In an embodiment, these surfactants are chosen from anionic or nonionic surfactants.

The surfactants preferably used in the composition according to the present disclosure are chosen: from nonionic surfactants: fatty acids, fatty alcohols, polyethoxylated or polyglycerolated fatty alcohols such as polyethoxylated stearyl or cetylstearyl alcohols, d esters fatty acid and sucrose, alkyl glucose esters, in particular fatty esters of $C_1$-$C_6$ alkyl glucose polyoxyethylenated, and mixtures thereof; and from among anionic surfactants: $C_{16}$-$C_{30}$ fatty acids neutralized by amines, ammonia or alkaline salts, and their mixtures.

In an embodiment, surfactants are used to make it possible to obtain an oil-in-water or wax-in-water emulsion.

The composition may comprise at least one second additional film-forming polymer, different from the first polymer described above.

In an embodiment, the second film-forming polymer is present in the composition according to the invention in a dry matter content ranging from 0.1% to 60% by weight relative to the total weight of the composition, preferably from 0.5% to 40% by weight, and better from 1% to 30% by weight.

As used herein, the term "film-forming polymer" means a polymer capable of forming on its own or in the presence of an auxiliary film-forming agent, a continuous and adherent film on a support, in particular on keratinous materials.

The composition may include a film-forming polymer capable of forming a hydrophobic film, that is to say a polymer whose film has a solubility in water at 25° C. of less than 1% by weight.

Among the film-forming polymers used in an embodiment, mention may be made of synthetic polymers, of radical type or of polycondensate type, polymers of natural origin, and mixtures thereof. As used herein, "radical film-forming polymer" means a polymer obtained by polymerization of unsaturated monomers, in particular ethylenic, each monomer being capable of homopolymerizing (unlike polycondensates).

The film-forming polymers of the radical type may in particular be vinyl polymers or copolymers, in particular acrylic polymers.

The vinyl film-forming polymers can result from the polymerization of ethylenically unsaturated monomers having at least one acid group and/or esters of these acid monomers and/or amides of these acid monomers.

As monomer carrying an acid group, it is possible to use unsaturated, alpha, s-ethylenic carboxylic acids such as acrylic acid, methacrylic acid, crotonic acid, maleic acid or itaconic acid. Preferably (meth) acrylic acid and crotonic acid are used, and more preferably (meth) acrylic acid.

The esters of acidic monomers are advantageously chosen from esters of (meth) acrylic acid (also called (meth) acrylates), in particular alkyl (meth) acrylates, in particular $C_1$-$C_{20}$ alkyl, of preferably in $C_1$-$C_{20}$, aryl (meth) acrylates, in particular $C_6$-$C_{10}$ aryl, hydroxyalkyl (meth) acrylates, in particular $C_2$-$C_6$ hydroxyalkyl.

Mention may be made, among alkyl (meth) acrylates, of methyl methacrylate, ethyl methacrylate, butyl methacrylate, isobutyl methacrylate, 2-ethylhexyl methacrylate, lauryl methacrylate, cyclohexyl methacrylate.

Among the hydroxyalkyl (meth) acrylates, there may be mentioned hydroxyethyl acrylate, 2-hydroxypropyl acrylate, hydroxyethyl methacrylate, 2-hydroxypropyl methacrylate.

Mention may be made, among aryl (meth) acrylates, of benzyl acrylate and phenyl acrylate.

Particularly preferred esters of (meth) acrylic acid are alkyl (meth) acrylates.

In an embodiment, the alkyl group of the esters are either fluorinated or perfluorinated, that is to say that some or all of the hydrogen atoms of the alkyl group are substituted by fluorine atoms.

As amides of the acidic monomers, mention may, for example, be made of (meth) acrylamides, and in particular N-alkyl (meth) acrylamides, in particular of $C_2$-$C_{12}$ alkyl. Among the N-alkyl (meth) acrylamides, there may be mentioned N-ethyl acrylamide, N-t-butyl acrylamide, N-t-octyl acrylamide and N undecylacrylamide.

The vinyl film-forming polymers can also result from the homopolymerization or from the copolymerization of monomers chosen from vinyl esters and styrene monomers. In an embodiment, these monomers are polymerized with acidic monomers and/or their esters and/or their amides, such as those mentioned above.

Examples of vinyl esters that may be mentioned include vinyl acetate, vinyl neodecanoate, vinyl pivalate, vinyl benzoate and vinyl t-butyl benzoate.

As styrene monomers, mention may be made of styrene and alpha-methyl styrene. It is possible to use any monomer known to a person skilled in the art falling within the categories of acrylic and vinyl monomers (including the monomers modified by a silicone chain).

Among the film-forming polycondensates, mention may be made of polyurethanes, polyesters, polyester amides, polyamides, and epoxy ester resins, polyureas.

In an embodiment, the polyurethanes are chosen from anionic, cationic, nonionic or amphoteric polyurethanes, polyurethanes-acrylics, polyurethanes-polyvinylpirrolidones, polyester-polyurethanes, polyether-polyurethanes, polyureas, polyurea-polyurethanes, and their mixtures.

In an embodiment, the polyesters are obtained, in a known manner, by polycondensation of dicarboxylic acids with polyols, in particular diols.

In an embodiment, the dicarboxylic acid are aliphatic, alicyclic or aromatic. Examples of such acids include: oxalic acid, malonic acid, dimethylmalonic acid, succinic acid, glutaric acid, adipic acid, pimelic acid, 2, 2 acid-dimethyllutaric, azelaic acid, suberic acid, Sebacic acid, fumaric acid, maleic acid, itaconic acid, phthalic acid, Dodecanedioic acid, 1,3 cyclohexanedicarboxylic acid, acid 1,4-cyclohexanedicarboxylic, isophthalic acid, terephthalic acid, 2,5-norborane dicarboxylic acid, diglycolic acid, thiodipropionic acid, 2,5-naphthalenedicarboxylic acid, acid 2,6-naphthalene. In an embodiment, these dicarboxylic acid monomers are used alone or in combination of at least two dicarboxylic acid monomers. Among these monomers, phthalic acid, isophthalic acid and terephthalic acid are preferably chosen.

In an embodiment, the diol is chosen from aliphatic, alicyclic and aromatic diols. Preferably, a diol chosen from: ethylene glycol, diethylene glycol, triethylene glycol, 1,3-propanediol, cyclohexane dimethanol, 4-butanediol is used.

In an embodiment, as other polyols, glycerol, pentaerythritol, sorbitol, trimethylol propane are used.

In an embodiment, the polyester amides are obtained in a similar manner to the polyesters, by polycondensation of diacids with diamines or amino alcohols.

As diamine, it is possible to use ethylenediamine, hexamethylenediamine, meta or para-phenylenediamine. In an embodiment, as amino alcohol, monoethanolamine is used.

In an embodiment, the polyester also comprises at least one monomer carrying at least one $SO_3M$ group, with M representing a hydrogen atom, an amonium ion $NH_4^+$ or a metal ion, such as for example a $Na^+$, $Li^+$, $K^+$, $Mg^{2+}$, $Ca^{2+}$, $Cu^{2+}$, $Fe^{2+}$, $Fe^{3+}$. One can use in particular a bifunctional aromatic monomer comprising such a group $—SO_3M$.

In an embodiment, the aromatic nucleus of the bifunctional aromatic monomer further carrying a group $—SO_3M$ as described above is chosen for example from benzene, naphthalene, anthracene, diphenyl, oxidiphenyl, sulfonyldiphenyl, methylenediphenyl nuclei. As an example of a bi-functional aromatic monomer further bearing an $—SO_3M$ group, there may be mentioned: sulfoisophthalic acid, Sulfoterephthalic acid, sulfophthalic acid, 4-sulfonaphthalene-2, 7 dicarboxylic acid.

It is preferred to use copolymers based on isophthalate/sulfoisophthalate, and more particularly copolymers obtained by condensation of di-ethylene glycol, cyclohexane dimethanol, isophthalic acid, sulfoisophthalic acid.

In an embodiment, the polymers of natural origin, optionally modified, are chosen from shellac resin, sandara gum, dammars, elemis, copals, cellulose polymers, and mixtures thereof.

According to a first embodiment of the composition according to the invention, the second film-forming polymer is present in the form of particles in aqueous dispersion, generally known under the name of latex or pseudolatex.

The techniques for preparing these dispersions are well known to those skilled in the art.

As an aqueous dispersion of film-forming polymer, it is possible to use the acrylic dispersions. As aqueous dispersion of film-forming polymer, it is also possible to use the polymer dispersions resulting from the radical polymerization of one or more radical monomers inside and/or partially on the surface, of preexisting particles of at least one chosen polymer. in the group consisting of polyurethanes, polyureas, polyesters, polyesteramides and/or alkydes. These polymers are generally called hybrid polymers.

In a second embodiment of the composition, the film-forming polymer is any suitable water-soluble polymer.

The size of the polymer particles dispersed in the aqueous phase can range from 5 nm to 600 nm, and preferably from 20 nm to 300 nm.

In some embodiments, the composition may comprise an auxiliary film-forming agent promoting the formation of a film with the film-forming polymer. In an embodiment, such a film-forming agent is chosen from all the compounds known to a person skilled in the art as being capable of fulfilling the desired function, and in particular are chosen from plasticizing agents and coalescing agents.

In some embodiments, the composition may also comprise a coloring material or any additive usually used in cosmetics such as antioxidants, fillers, preservatives, perfumes, neutralizers, thickeners, cosmetic or dermatological active agents such as, for example, emollients, moisturizers, vitamins, sun filters, and mixtures thereof. In an embodiment, these additives are present in the composition in a content ranging from 0% to 20% (in particular from 0.01% to 20%) of the total weight of the composition and better still from 0.01% to 10% (if present).

In some embodiments, the composition is a cosmetic composition as disclosed in U.S. Patent Application Publication No. 2015/0174056 "COSMETIC COMPOSITION FOR COATING KERATIN FIBERS," filed by Barba et al. and currently assigned to L'Oreal SA, the disclosure of which is incorporated herein in its entirety.

In some embodiments, the composition is a cosmetic composition as disclosed in U.S. Patent Application Publication No. 2002/0168335 "COSMETIC COMPOSITION COMPRISING A WAX AND A POLYMER," filed by Nathalie Collin and currently assigned to L'Oreal SA, the disclosure of which is incorporated herein in its entirety.

In some embodiments, the composition is a cosmetic composition as disclosed U.S. Pat. No. 7,410,636 "COSMETIC COMPOSITION COMPRISING A POLYMER AND FIBRES," issued to Nathalie Collin and currently assigned to L'Oreal SA, the disclosure of which is incorporated herein in its entirety.

The use of a polymer with a particular amide unit in a composition comprising a wax-in-water emulsion makes it possible to improve the adhesion properties of the composition on keratinous materials, in particular on keratin fibers such as eyelashes. The composition is easily applied to keratinous materials and allows the composition to be deposited quickly in sufficient quantity to obtain a makeup having the expected cosmetic properties. In particular, a thick deposit of make-up is quickly obtained on the keratinous materials, which prevents users from applying the composition for too long to the keratinous materials.

The level of wax in the emulsion provides a creaminess and texture well-suited for mascara. In some embodiments a preferred ratio gives a viscosity range from 10,000 cps to 20,000 cps. This range has been found to give the superior depositing and buildability characteristics.

Figure 2:
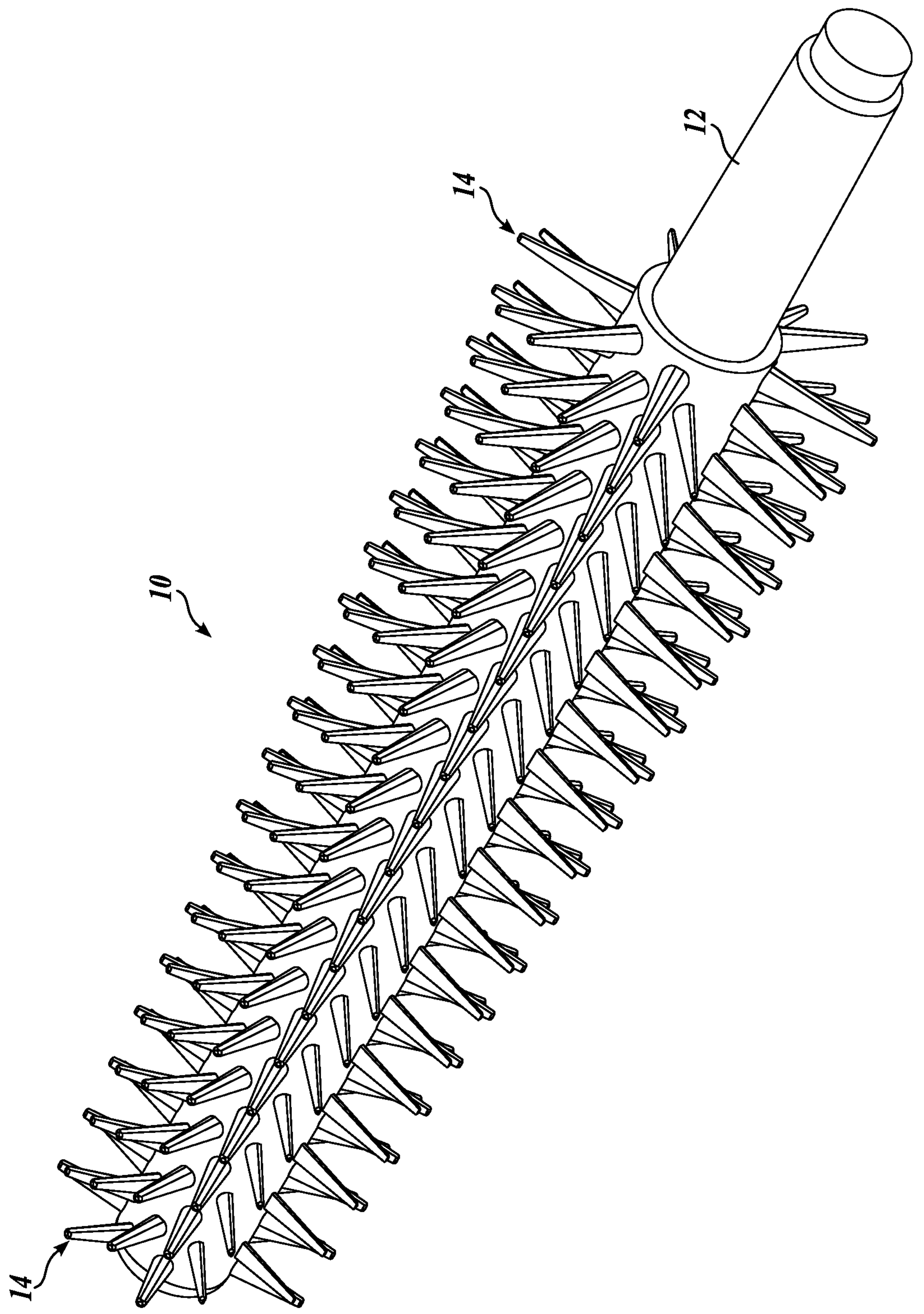
FIG. 2 shows an isometric view of a representative embodiment of an applicator included with the kit shown in FIG. 1.
Figure 3:
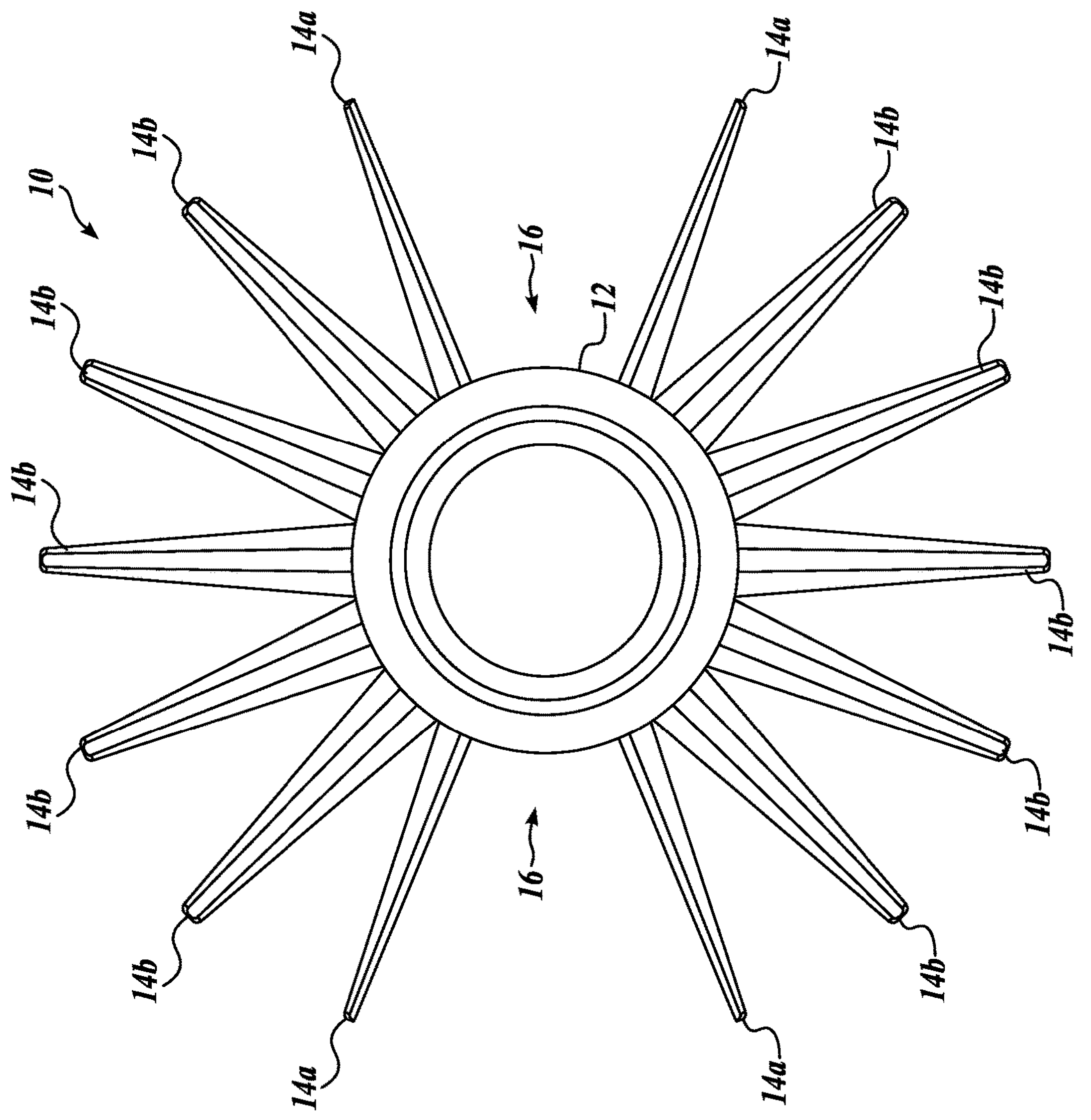
FIG. 3 shows an end view of the applicator shown in FIG. 2.

FIGS. 2 and 3 show a representative embodiment of the brush 10 shown in FIG. 1, which has been found to be particularly suitable for applying the described cosmetic composition. The brush 10 includes an elongate core 12 with a plurality of bristles 14 extending radially therefrom. The bristles 14 (indicated as 14a and 14b in FIG. 3) are spaced around the circumference of the core 12 to form a plurality of longitudinal rows. In the illustrated embodiment, the rows of bristles 14b are evenly spaced from adjacent rows of bristles. One or more pairs of adjacent rows of bristles 14a are spaced farther apart from each other than the other rows of bristles 14b so that adjacent rows of bristles 14a form a reservoir 16 between the rows. The reservoir 16 extend in a longitudinal direction and provide an area that receives the cosmetic composition when the brush 10 is immersed in the compositions. In some embodiments, the brush 10 includes a single reservoir 16. In some embodiments, the brush 10 includes two or more reservoirs 16, Referring back to FIG. 1, the aperture 56 of the wiper 54 is sized relative to the brush 10 to control the amount of the cosmetic composition 60 "loaded" on the brush when the brush is withdrawn from the container 50. In this regard, excess amounts of the cosmetic composition 60 are removed from the brush 10 as the brush passes through the aperture 56 such that the outer diameter of the cosmetic composition is approximately the diameter of the aperture. In some embodiments, the wiper 54 is made from polyethylene, polypropylene, acrylonitrile butadiene rubber (nitrile rubber), thermoplastic elastomers, or any suitable material or combination of materials. In some embodiments, the wiper 54 flexes slightly when the brush 10 passes through the aperture 56 so that the resulting diameter of the cosmetic composition 60 is slightly larger than the diameter of the aperture.

The brush 10 and the wiper 54 are configured to provide a layer of cosmetic composition 60 having a nominal thickness within a desired range. The nominal thickness is generally defined as the ½ of the difference between the diameter of the aperture 56 and the diameter of the core 12 of the brush 10. In some embodiments, the core 12 of the brush 10 has a diameter of 2 mm, and the aperture 56 has a diameter of 4.5 mm, so that the nominal thickness of the cosmetic composition 60 is approximately 1.25 mm. In some embodiments, deflection of the wiper 54 results in a slightly larger nominal thickness, for example in the range of 1.2 mm to 1.5 mm or 1.4 mm to 1.5 mm. In some embodiments, the aperture 56 has a diameter in the range of 4.0 mm to 5.0 mm.

With the brush "loaded" with the cosmetic composition, i.e., when the reservoirs 16 are at least partially filled with the composition, a user strokes the brush 10 along the lashes. The bristles 14 stroke through, i.e., separate and extend through and separate, the lashes while depositing the cosmetic composition thereon. As the brush 10 is moved toward the end of the lash, i.e., away from the eye lid, the cosmetic composition coat, thickens, and lengthens (elongates) the lashes.

The bristles 14 are formed from a thermoplastic elastomer (TPE) having a hardness in the range of 32 shore D to 38 shore D. In some embodiments, the core 12 and at least some of the bristles 14 are integrally formed. In some embodiments, the number, location, and shape(s) of the bristles 14 varies. In some embodiments, the bristles 14 are formed from a first material, and the core 12 is formed from a separate material, wherein the second material has a higher shore D hardness than the first material.

In some embodiments, the flexibility of the bristles 14 or rows of bristles varies. In some embodiments, the bristles 14 or rows of bristles are formed from different materials. In some embodiments, some of the bristles 14 or rows of bristles are formed by bi-injection of different materials to increase or decrease the rigidity of the bristles.

In some embodiments, the bristles are configured to have different shapes to provide different flexibilities. In some embodiments, at least a portion of the cross-section of each bristle has the shape of a circle, a semi-circle, an oval, a square, a rectangle, a polygon, or any other suitable shape. The shape of the bristle affects the flexibility of the bristle. For example, a semi-circle is more rigid (less flexible) than a circle; an oval has different stiffnesses along the major axis and the minor axis, a rectangle has a more rigid base, etc.

In some embodiments, the rigidity of the rows follows a set pattern. For example, in some embodiments, every fourth row is more rigid than the remaining rows. These and other variations in the bristle flexibility are contemplated and should be considered within the scope of the present disclosure.

In some embodiments, the core 12 and the bristles 14 are separately formed and then joined by mechanical fasteners, interference fits, adhesives, or other suitable means. In some embodiments, the core 12 and bristles 14 are manufactured by overmolding, insert molding, or any other suitable manufacturing process.

In some embodiments, the bristles 14 comprise thermoplastic elastomers (TPEs), including styrene-ethylene-butylene-styrene (SEBS), HYTREL, other suitable TPEs, and/or mixture thereof.

In addition to having a hardness in the range of 32 shore D to 38 shore D, the bristle material is preferably configured to provide the bristles 14 with bend recovery in the range of 90% to 100%. With respect to nylon and other thermoplastic materials, "bend recovery" is an indication of the material's "memory." In a brush filament, the bend recovery is the tendency for a deflected filament to return to its original deployment. The bend recovery for nylon is generally over 90%, i.e., the filament returns to about 90% of its original deployment after being deflected.

For previously known cosmetic compositions, brushes having bristles with a hardness in the range of 45 shore D to 55 shore D were utilized because using softer brushes, e.g., brushes having a hardness in the range of 32 shore D to 38 shore D was not feasible. In this regard, brushes with softer bristles were not effective because the bristles were too soft to work with typical formulations that were thick enough to require a stronger stroking motion. More specifically, softer bristles flex too much to effectively deposit the cosmetic composition onto the lash.

It was discovered, however, that a cosmetic composition comprising a wax emulsion and a polymer in the manner of the described embodiments achieved unexpectedly superior application results using a brush having a hardness in the range of 32 shore D to 38 shore D. Contrary to conventional views, it was discovered that a soft bristle material provides improved application of the disclosed cosmetic compositions because the formulation is creamy enough to create just the right amount of flexing of brush the core relative to the pressure against lashes, with the bristles being more flexible than traditional brushes. As a result, the bristles adjust to the various angles that lashes create during stroking, making the brush more adaptive so that the cosmetic composition is deposited evenly across the lashes.

While illustrative embodiments have been illustrated and described, it will be appreciated that various changes can be made therein without departing from the spirit and scope of the invention.

The embodiments of the invention in which an exclusive property or privilege is claimed are defined as follows:

1. A mascara packaging set, comprising:
- a container with a wiper having an aperture;
- a mascara composition disposed within the container and including a wax emulsion, at least one polymer, and fibers, the mascara composition having a viscosity in a range of 10,000 cps to 20,000 cps; and
- an applicator configured to extend into the container through the aperture, the applicator having an elongate core and a plurality of bristles extending radially therefrom, at least one of the bristles being formed from a thermoplastic elastomer having a hardness in the range of 32 shore D to 38 shore D, the plurality of bristles forming rows along the core in an axial direction, wherein:
- rows of a first pair of adjacent rows are spaced apart from each other at a first distance along a circumferential direction to define a first channel such that none of the plurality of bristles is positioned in the first channel,
- rows of a second pair of adjacent rows are spaced apart from each other at a second distance along the circumferential direction to define a second channel opposite the first channel such that none of the plurality of bristles is positioned in the second channel, and
- a plurality of intermediate rows are circumferentially positioned between the first and second channels, each of the plurality of intermediate rows being spaced apart from an adjacent rows on each side at a third distance along the circumferential direction, the first distance and the second distance being larger than the third distance.

2. The mascara packaging set of claim 1, wherein the bristles from the first pair of adjacent rows have a semi-circular cross-sectional area.

3. The mascara packaging set of claim 2, wherein the bristles from the plurality of intermediary rows have polygonal cross-sectional area.

4. The mascara packaging set of claim 2, wherein the bristles from the second pair of rows have circular cross-sectional area.

5. The mascara packaging set of claim 2, wherein the bristles from the second pair of adjacent rows have a semi-circular cross-sectional area.

6. The mascara packaging set of claim 1, wherein the aperture of the wiper is sized to limit a thickness of a layer of mascara composition on the brush to a predetermined maximum thickness when the brush is removed from the container.

7. The mascara packaging set of claim 6, wherein the maximum thickness is in the range of 1.20 mm to 1.50 mm.

8. The mascara packaging set of claim 7, wherein the aperture has a diameter in the range of 4.00 mm to 5.00 mm.

9. The mascara packaging set of claim 1, wherein at least one row of bristles is formed from a different material than at least one of the other rows of bristles.

10. The mascara packaging set of claim 9, wherein the at least one row of bristles is more rigid than the at least one of the other rows of bristles.

11. The mascara packaging set of claim 10, wherein the at least one row of bristles is formed by the thermoplastic elastomer and a second material.

12. The mascara packaging set of claim 10, wherein the second material has a hardness greater than the hardness of the thermoplastic elastomer.

13. The mascara packaging set of claim 1, wherein the wax emulsion comprises a water-in-wax emulsion.

14. The mascara packaging set of claim 1, wherein the polymer has a weight-average molecular mass of less than 100,000.

15. The mascara packaging set of claim 1, wherein the polymer has a weight-average molecular mass of less than 50,000.

16. The mascara packaging set of claim 1, wherein the first distance is equal to the second distance.

17. The mascara packaging set of claim 16, wherein the bristles from the plurality of intermediary rows have polygonal cross-sectional area.

* * * * *